United States Patent [19]

Terada et al.

[11] 4,319,485

[45] Mar. 16, 1982

[54] TEMPERATURE-HUMIDITY DETECTING APPARATUS

[75] Inventors: Jiro Terada; Tsuneharu Nitta, both of Katano, Japan

[73] Assignee: Matsushita Electric Industrial Co., Ltd., Kadoma, Japan

[21] Appl. No.: 107,183

[22] Filed: Dec. 26, 1979

[30] Foreign Application Priority Data

Dec. 28, 1978 [JP] Japan .................. 53-163478
Dec. 28, 1978 [JP] Japan .................. 53-163479
Jun. 9, 1979 [JP] Japan .................. 54-72548
Jun. 9, 1979 [JP] Japan .................. 54-72549
Jun. 9, 1979 [JP] Japan .................. 54-72550
Jun. 9, 1979 [JP] Japan .................. 54-72558

[51] Int. Cl.³ ........................................... G01W 27/02
[52] U.S. Cl. ..................................... 73/336; 73/336.5;
    73/344; 338/25; 338/35; 340/584; 340/602
[58] Field of Search ................. 73/344, 343 R, 336.5,
    73/336, 170; 338/35, 25; 200/61.06; 361/282,
    286; 324/65 R; 340/584, 602

[56] References Cited

U.S. PATENT DOCUMENTS

| | | | |
|---|---|---|---|
| 2,444,030 | 6/1948 | Burch | 340/602 X |
| 2,444,111 | 6/1948 | Pear, Jr. | 324/71 R |
| 2,684,592 | 7/1954 | Hadady | 73/336.5 |
| 2,733,607 | 2/1956 | Miller | 73/336.5 |
| 2,975,638 | 3/1961 | Morrison | 73/336.5 |
| 3,196,682 | 7/1965 | Johnson, Jr. | 73/336.5 |
| 3,599,862 | 8/1971 | Hogan et al. | 73/336.5 X |
| 3,872,419 | 3/1975 | Groves et al. | 338/25 |
| 3,934,111 | 1/1976 | Roselli et al. | 340/602 X |
| 4,078,431 | 3/1978 | Mott | 73/344 X |

Primary Examiner—C. L. Albritton
Attorney, Agent, or Firm—Wenderoth, Lind & Ponack

[57] ABSTRACT

A temperature-humidity detecting apparatus which can detect the temperature and humidity with a single element. The temperature-humidity detecting element of the present invention varies its impedance value with respect to variations in the temperature and humidity, and the temperature-humidity detecting apparatus is adapted to detect the variations in the temperature-humidity detecting element impedance to determine the temperature and humidity.

4 Claims, 14 Drawing Figures

TEMPERATURE-HUMIDITY DETECTING APPARATUS

BACKGROUND OF THE INVENTION

The present invention relates to a temperature-humidity detecting apparatus for use in the detection of the ambient temperature and humidity using an element which is sensitive to changes in both temperature and humidity.

Generally, humidity detecting resistor elements are used for humidity detection and thermoelectric couples or thermistors are used for temperature detection. The humidity detecting resistor is sensitive to the ambient humidity so as to vary the resistance value in accordance therewith and is used as a humidity measuring element or as a sensor for humidity regulating applications. As is known, the humidity detecting resistor is made of metallic oxides, superior in moisture absorption, such as $Fe_2O_3$, $Al_2O_3$, etc. In most cases, the various appliances must detect not only the humidity, but also the temperature. The air conditioning facilities must simultaneously effect both comfortable temperatures and a healthy humidity. Accordingly, in the conventional devices, both a temperature detecting element and a humidity detecting element were used to detect the temperature and the humidity, and the respective circuits were constructed independently to provide the two-system circuit structure to meet the requirements, resulting in a circuit construction which became complicated, thus resulting in higher cost.

SUMMARY OF THE INVENTION

Accordingly, a principal object of the present invention is to provide a circuit element which is free from the conventional disadvantages and can control the temperature and humidity by a single element.

Another object of the present invention is to provide a temperature-humidity detecting apparatus which can vary the power supply frequency applied to the detecting element to detect both the temperature and humidity at the same time.

According to the present invention, the signals corresponding to the ambient temperature and humidity are adapted to be detected from the electrode face of a humidity detecting resistor element composed of a dielectric having a temperature dependency. In such elements, the impedance through the dielectric capacitance component of an oxide material is high when the applied power supply frequency is in a low frequency zone. In addition, impedance variations due to humidity variations is predominant more than that due to the impedance through the dielectric capacitance component. Accordingly, the humidity can be detected by the elements as a humidity detecting unit in the low frequency zone. On the contrary, in the high frequency zone, the impedance through the dielectric capacitance component becomes lower and the temperature detection is independent of the variations in humidity. Accordingly, the temperature dependency of the dielectric constant through variations in temperature becomes predominant, and the elements can be used as a temperature detector to detect the temperature in the high frequency zone. Also, the temperature-humidity detecting apparatus comprises in combination of the above element, a load inpedance source with frequency to be selected and a power supply circuit connected to said element and source.

BRIEF DESCRIPTION OF THE DRAWINGS

These and other objects, features, aspects and advantages of the present invention will become more apparent from the following detailed description of the present invention when taken in conjunction with the accompanying drawings in which.

DESCRIPTION OF PREFERRED EMBODIMENTS

Figure 1:
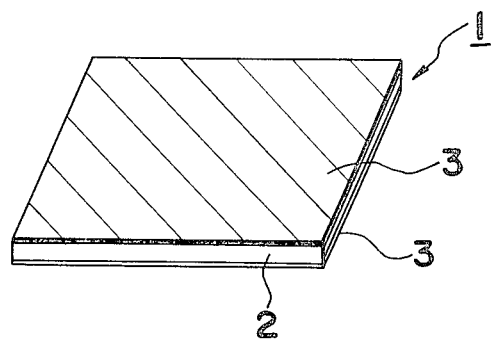
FIG. 1 is a perspective view showing a temperature-humidity detecting element used with the present invention.

According to the present invention, as starting raw materials for the temperature-humidity detecting element, a component which was composed of $BaCO_3$ in an amount of 0.5 mol %, $TiO_2$ in an amount of 1 mol %; and $SrCO_3$ in an amount of 0.5 mol %, and which was wet mixed and dried into a powder. The resultant powdered material was pressed into a shape $4 \times 4 \times 0.25$ mm under a molding pressure of $7.5 \times 10^6$ kg/m². Thereafter, the resultant plate was fired at the temperature of 1,250° C., and a pair of electrodes 3 and 3 of $RuO_2$ series material were mounted on the fired plate 2, as shown in FIG. 1, to provide an element 1. The element 1 was examined, in terms of humidity characteristics, temperature characteristics and frequency-electric impedance characteristics between the electrodes 3 and 3 thereof. The results are shown in FIG. 2, FIG. 3 and FIG. 4.

Figure 2:
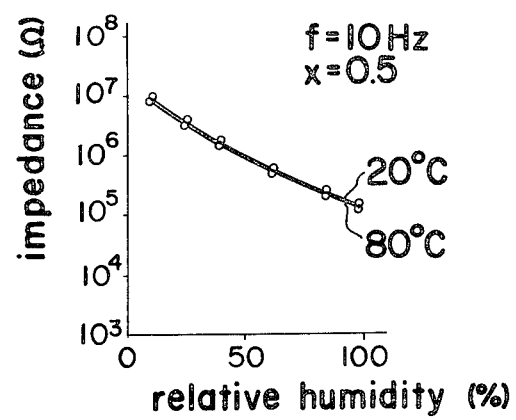
FIG. 2 shows the humidity detecting characteristics of the temperature-humidity detecting element used in one embodiment of the present invention.

FIG. 2 shows that the electric impedance varies with the varying relative humidity in the low frequency zone (10 Hz) and temperature variations (20° C. and 80° C) hardly influence the variation in the electric impedance.

Figure 3:
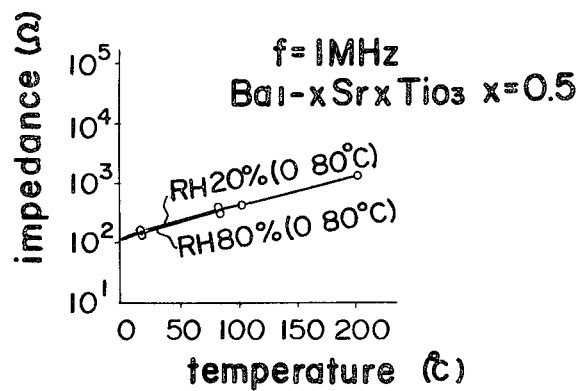
FIG. 3 shows a temperature characteristic graph of the temperature-humidity detecting element used in the above-noted one embodiment.

FIG. 3 shows that the electric impedance varies with the varying temperatures in the high frequency zone (1 MHz) and the humidity variations (20% and 80%) hardly influence the variation in the electric impedance.

Figure 4:
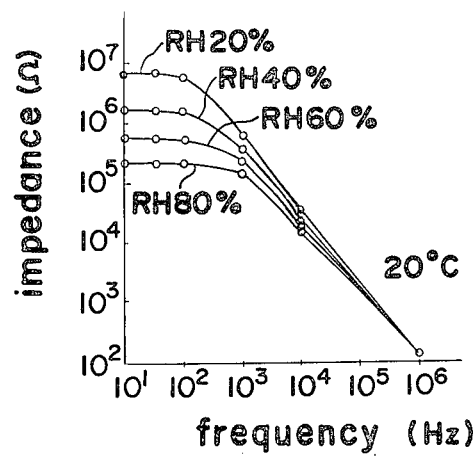
FIG. 4 shows a frequency characteristic graph of the temperature-humidity detecting element used in one embodiment.

FIG. 4 shows that the variation in the humidity (20%, 40%, 60% and 80%) influences the electric impedance in the low frequency zone ($10^3$ Hz), but the variation in the humidity hardly influences the electric impedance in the high frequency zone ($10^5$ Hz).

The result shown in FIG. 2 through FIG. 4 show that both the humidity and the temperature can be detected by a single specimen element 1. In other words, the humidity can be detected in the low frequency zone with respect to the element 1 and the temperature can be detected in the high frequency zone thereof.

Figure 5:
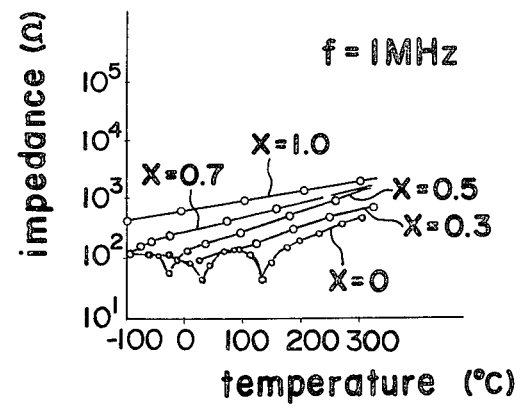
FIG. 5 shows a temperature characteriztic graph with the variations of the component included in the temperature-humidity detecting element.
Figure 6:
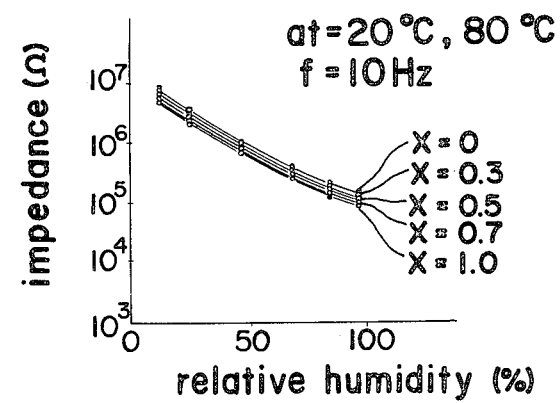
FIG. 6 shows a humidity detection characteristic graph with the variations of the component included in the temperature. humidity detecting element.

The value of x in $(Ba_{1-x}Sr_x)TiO_3$ component in the element 1 was variably changed within the range of 0 through 1 to examine the temperature-impedance characteristics and the humidity-impedance characteristics and the results are obtained as shown in FIG. 5 and FIG. 6, when X was 0, 0.3, 0.5, 0.9, and 1.0 in $(Ba_{1-x}Sr_x-)TiO_3$.

According to FIG. 5, the relationship between the temperature and the impedance is approximately linear in logarithmic scale of the impedance when x in $(Ba_{1-x}Sr_x)TiO_3$ is 0.5 or more at the temperatures of 0° C. or more, while, the peaks appear at different temperatures due to the value of x within the range of x=0 to 1. These peaks are curie points for $(Ba_{1-x}Sr_x)TiO_3$, so that the range of the temperature detection, i.e. the desired detection temperature range can be obtained at the temperature of the curie point or higher with the linear relationship between the temperature and impedance.

FIG. 6 shows that the characteristic variations are hardly recognised due to X=0 to 1, and the variation in the temperature hardly influences the variation in the impedance. The results of FIG. 6 was obtained on the application of 10 Hz.

The composition of the temperature-humidity detecting element is not restricted to the component of the $Ba_{1-x}Sr_xTiO_3$ (x=0 to 1). Addition of at least one compound selected from compounds such as $MgCr_2O_4$, $CaTiO_3$, $BaZrO_3$, the other perobskite type, tungsten bronze type, pyroclower type, spinel type and metallic oxides to the $Ba_{1-x}Sr_xTiO_3$ can provide an element, which is quicker in response, has much less characteristic deterioration, has a higher sensitivity, and is superior in the temperature and humidity separation during the detection of the temperature and the humidity.

Also, the element of the present invention is superior in its thermal resistance, and, if and when the element is contaminated by suspended particles in the air, heating and cleaning operations can be performed to remove the contamination.

The temperature-humidity detecting element composed of an oxide portion and having, as major component, the component shown in $PbxO_3$, will be described hereinafter in another embodiment of the present invention. As in the temperature-humidity detecting element with the above-described $Ba_{1-x}Sr_xTiO_3$ component as major component, a starting material, which was composed of PbO, MgO and $Nb_2O_5$, was wet-mixed and thereafter dried into powder. The resultant powdered material was molded under (molding pressure of $7.5 \times 10^6$ kg/m² into a plate of 4×4×0.25 mm and an oxide porcelain of $Pb(Mg_{1/3}Nb_{2/3})O_3$ was produced as a sintered product 2 as shown in FIG. 1. Then, $RuO_2$ series electrode paste was applied on the sintered product 2 and was baked at 800° C. to form the electrodes 3 and 3 thereby to construct a temperature-humidity detecting element 1.

Even in the other composition shown in the $PbxO_3$, the same thing can be applied to provide the temperature-humidity detecting element.

The characteristics of the temperature-humidity detecting element with the $Pb(Mg_{1/3}Nb_{2/3})O_3$ as major component will be described hereinafter according to the experiment results.

Figure 7:
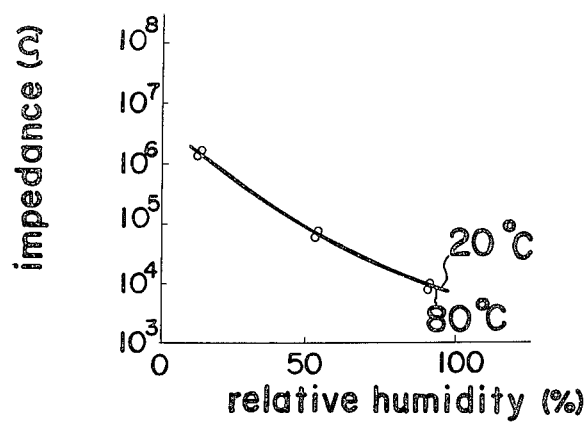
FIG. 7 shows a humidity detection characteristic graph upon the variations of electric impedance applied to the temperature-humidity detecting element in another embodiment of the present invention.

The graph of FIG. 7 shows the variations in the electric impedance accompanied by the variations in the relative humidity of the temperature-humidity detecting element when the low frequency power supply of 10 Hz-1V has been applied between the electrodes 3 and 3 at the temperature of 20° C. The electric impedance decreases with the increasing humidity. Also, according to the characteristic experiments performed at the temperature of 80° C. under the conditions of the same impressed power supply, no influences result due to the difference in temperatures. The result shows that, in the temperature-humidity detecting element, the variation in the electric impedance depends upon the humidity only under the conditions where the low frequency power supply has been applied to the element.

Figure 8:
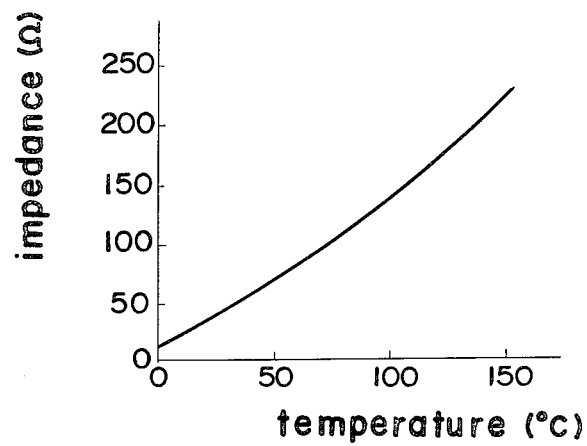
FIG. 8 shows a temperature characteristic graph upon the variation of electric impedance applied to the temperature. humidity detecting element in the above-noted another embodiment.
Figure 9:
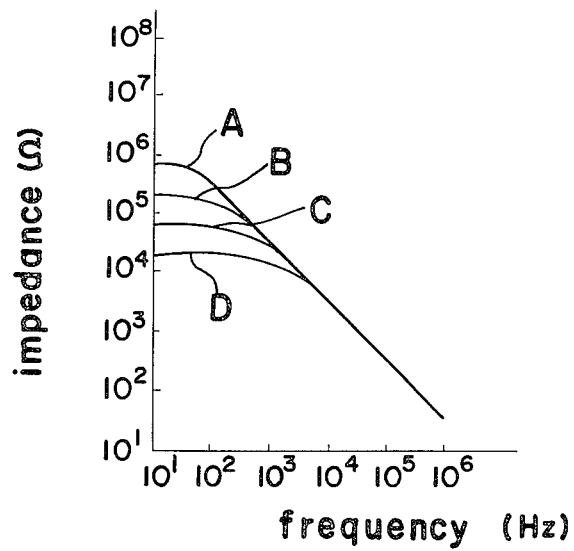
FIG. 9 shows a frequency characteristic graph upon the variation of electric impedance applied to the temperature-humidity detecting element in another embodiment.

The graph of FIG. 8 shows the variations in the electric impedance of the temperature-humidity detecting element accompanied through the variation in the temperature when the high frequency power supply of 1,000 KHz-1V has been applied between the electrode 3 and 3 at the humidity 50% by RH (1 through 95° C.). The electric impedance varies in accordance with the variation in the temperature, and the characteristics remains almost unchanged even when the relative humidity has been made 20% (0° to 80° C.) and 80% (0° to 80° C.) under the conditions of the same impressed power supply. The graph of FIG. 9 shows the frequency-electric impedance characteristic at the temperature of 20° C. where the humidity has been made a parameter in such a manner that reference character A shows characteristics with 20% RH, B with 40% RH, C with 60% RH and D with 80% RH, respectively, in humidity. No influences through the humidity variations in FIG. 9 are shown in the high frequency zone.

The above experiment results show that, in the temperature-humidity detecting element of the present invention, the variation in the electric impedance depend upon the humidity under the low frequency power supply impressing conditions and the variations in the electric impedance depends upon the temperature under the high frequency power supply impressing conditions.

Although in the above-described embodiment, a component of $Pb(Mg_{1/3}Nb_{2/3})O_3$ is employed, the temperature-humidity detecting element is not restricted, however, in construction to the above component. The experiments show that the same effect is provided even in a case where the component shown in $PbXO_3$ is used as a major component, wherein the X shall be component containing at least one of $(Mg_{1/2}W_{1/2})$, $(Cd_{1/2}W_{1/2})$, $(Co_{1/2}W_{1/2})$, $(Sc_{1/2}Nb_{1/2})$, $(Fe_{1/2}Nb_{1/2})$, $(In_{1/2}Nb_{1/2})$, $(Yb_{1/2}Nb_{1/2})$, $(Ho_{1/2}Nb_{1/2})$, $(Fe_{1/2}Ta_{1/2})$, $(Sc_{1/2}Ta_{1/2})$, $(Lu_{1/2}Nb_{1/2})$, $(Lu_{1/2}Ta_{1/2})$, $(Zn_{1/3}Nb_{2/3})$, $(Co_{1/3}Nb_{2/3})$, $(Ni_{1/3}Nb_{2/3})$, $(Mg_{1/3}Ta_{2/3})$, $(Co_{1/3}Ta_{2/3})$, $(Ni_{1/3}Ta_{2/3})$, $(Fe_{2/3}W_{1/3})$, $(Mn_{2/3}W_{1/3})$.

The experiment results are shown in Table 1 with respect to the temperature and humidity characteristics of each of the temperature-humidity detecting elements.

TABLE I

| | Major Component | Humidity characteristics ($\psi$) 20° C. 1MHz | 50% RH (1-95° C.) 150° C. | Temperature characteristics ($\psi$) 20% RH | at 20° C. 10 Hz 80% RH |
|---|---|---|---|---|---|
| 1 | $Pb(Mg_{\frac{1}{3}}W_{\frac{1}{3}})O_3$ | $3.8 \times 10^3$ | $7 \times 10^3$ | $2.1 \times 10^7$ | $4.1 \times 10^5$ |
| 2 | $Pb(Cd_{\frac{1}{3}}W_{\frac{1}{3}})O_3$ | $4.0 \times 10^3$ | $1.8 \times 10^3$ | $2.0 \times 10^7$ | $1.5 \times 10^5$ |
| 3 | $Pb(Co_{\frac{1}{3}}W_{\frac{1}{3}})O_3$ | $2.8 \times 10^3$ | $1.5 \times 10^3$ | $2.5 \times 10^7$ | $7.5 \times 10^5$ |
| 4 | $Pb(Sc_{\frac{1}{3}}Nb_{\frac{1}{3}})O_3$ | $5.6 \times 10^2$ | $1.0 \times 10^2$ | $7.0 \times 10^6$ | $5.0 \times 10^4$ |
| 5 | $Pb(Fe_{\frac{1}{3}}Nb_{\frac{1}{3}})O_3$ | $1.8 \times 10^2$ | $2.5 \times 10^1$ | $3.0 \times 10^6$ | $3.4 \times 10^4$ |
| 6 | $Pb(In_{\frac{1}{3}}Nb_{\frac{1}{3}})O_3$ | $9.3 \times 10^2$ | $5.0 \times 10^2$ | $1.6 \times 10^7$ | $5.9 \times 10^4$ |
| 7 | $Pb(Yb_{\frac{1}{3}}Nb_{\frac{1}{3}})O_3$ | $1.5 \times 10^4$ | $4.6 \times 10^3$ | $4.6 \times 10^7$ | $1.0 \times 10^5$ |
| 8 | $Pb(Ho_{\frac{1}{3}}Nb_{\frac{1}{3}})O_3$ | $3.5 \times 10^3$ | $1.8 \times 10^3$ | $3.2 \times 10^7$ | $1.0 \times 10^5$ |
| 9 | $Pb(Fe_{\frac{1}{3}}Ta_{\frac{1}{3}})O_3$ | $1.4 \times 10^2$ | $5.6 \times 10^2$ | $6.0 \times 10^6$ | $5.0 \times 10^4$ |
| 10 | $Pb(Sc_{\frac{1}{3}}Ta_{\frac{1}{3}})O_3$ | $1.8 \times 10^2$ | $5.6 \times 10^2$ | $4.3 \times 10^6$ | $3.0 \times 10^4$ |
| 11 | $Pb(Lu_{\frac{1}{3}}Nb_{\frac{1}{3}})O_3$ | $4.0 \times 10^3$ | $2.2 \times 10^3$ | $2.1 \times 10^7$ | $2.0 \times 10^5$ |
| 12 | $Pb(Lu_{\frac{1}{3}}Ta_{\frac{1}{3}})O_3$ | $4.6 \times 10^3$ | $2.8 \times 10^3$ | $5.2 \times 10^7$ | $2.1 \times 10^5$ |
| 13 | $Pb(Mg_{\frac{1}{3}}Nb_{\frac{2}{3}})O_3$ | $3.0 \times 10^1$ | $2.2 \times 10^2$ | $8.9 \times 10^5$ | $2.2 \times 10^4$ |
| 14 | $Pb(Zn_{\frac{1}{3}}Nb_{\frac{2}{3}})O_3$ | $1.4 \times 10^2$ | $1.4 \times 10^1$ | $1.1 \times 10^6$ | $9.9 \times 10^3$ |
| 15 | $Pb(Co_{\frac{1}{3}}Nb_{\frac{2}{3}})O_3$ | $6.0 \times 10^1$ | $8.0 \times 10^1$ | $1.2 \times 10^6$ | $2.1 \times 10^4$ |
| 16 | $Pb(Ni_{\frac{1}{3}}Nb_{\frac{2}{3}})O_3$ | $4.0 \times 10^2$ | $1.1 \times 10^3$ | $9.5 \times 10^6$ | $2.0 \times 10^5$ |
| 17 | $Pb(Mg_{\frac{1}{3}}Ta_{\frac{2}{3}})O_3$ | $9.3 \times 10^1$ | $1.4 \times 10^3$ | $8.8 \times 10^6$ | $1.1 \times 10^5$ |
| 18 | $Pb(Co_{\frac{1}{3}}Ta_{\frac{2}{3}})O_3$ | $1.4 \times 10^2$ | $9.1 \times 10^1$ | $8.2 \times 10^6$ | $9.1 \times 10^3$ |
| 19 | $Pb(Ni_{\frac{1}{3}}Ta_{\frac{2}{3}})O_3$ | $3.1 \times 10^2$ | $2.0 \times 10^2$ | $9.1 \times 10^6$ | $1.2 \times 10^5$ |
| 20 | $Pb(Fe_{\frac{2}{3}}W_{\frac{1}{3}})O_3$ | $1.4 \times 10^2$ | $5.6 \times 10^2$ | $7.8 \times 10^6$ | $6.8 \times 10^4$ |
| 21 | $Pb(Mn_{\frac{2}{3}}W_{\frac{1}{3}})O_3$ | $1.5 \times 10^2$ | $7.3 \times 10^1$ | $1.4 \times 10^7$ | $2.9 \times 10^4$ |

The composition of the temperature-humidity detecting element is not restricted to the component of the $PbXO_3$. Use of of at least one compound selected from compounds such as $BaTiO_3$, $SrTiO_3$, $PbTiO_3$, $CaTiO_3$, $PbZrO_3$, $KNbO_3$, $NaNbO_3$, $LiNbO_3$, $LiTaO_3$, $Pb(Mg_{1/3}Nb_{2/3})O_3$ and the other probskite type, tungsten bronze type, pyroclower type, spinel type and metallic oxides to the $PbXO_3$ can provide an element, which is quicker in response, extremely has less characteristic deterioration, has a higher sensitivity, and is superior in the temperature and humidity separation during the detection of the temperature and the humidity. The other filling materials can be added to the element to control the characteristics so that the higher sensitivity may be provided within a limited humidity or temperature detecting range. Also, the element of the present invention is superior in its thermal resistance, and, if and when the element is contaminated with suspended particles in the air, a heating and cleaning operation can be performed to remove the contamination. In addition, the element is not restricted in size, shape and construction, to other above-described embodiment and the various sizes and shapes can be provided.

The further embodiment of the present invention is a temperature-humidity detecting element composed of an oxide portion having the components represented in $ABO_3$ as major component, within AB is a component containing at least one from among KTa, PbHf, LiTa, LiNb, CaTi, PbZr, NaNb, KNb and PbTi. In the embodiment, a starting material, which was composed of PbO and $TiO_2$, was wet-mixed and thereafter was dried into powder. The resultant powdered material was molded under molding pressure of $7.5 \times 10^6$ kg/m² into a plate $4 \times 4 \times 0.25$ mm and was fired at 1,150° C. for two hours thereby to produce the oxide portion of $PbTiO_3$ as a sintered product 2 as in FIG. 1. Then, $RuO_2$ series electrode paste was applied on the sintered product 2 for a baking operation at 800° C., and electrodes 3 and 3 were formed to obtain a temperature-humidity detecting element 1. Also, the same method described above was applied for the other materials among $KTaO_3$, $PbHfO_3$, $LiTaO_3$, $LiNbO_3$, $CaTiO_3$, $PbZrO_3$, $NaNbO_3$ and $KNbO_3$ to be employed as the other starting material, with the construction such that electrode faces were provided on the oxide portion with the above-described components as major components so as to obtain the temperature-humidity detecting element, the characteristics of which will be described hereinafter.

Figure 10:
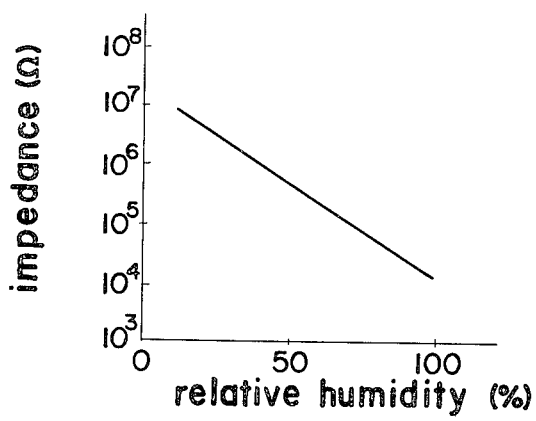
FIG. 10 shows a humidity detection characteristic graph upon the variations of electric impedance applied to the temperature-humidity detecting element in a further embodiment of the present invention.

The graph of FIG. 10 shows the variations in the electric impedance accompanied by the variations in the relative humidity of the temperature, humidity detecting element when the low frequency power supply of 10 Hz-1V has been applied between the electrodes 3 and 3 at the temperature of 20° C. with a result such that the electric impedance decreases with the increasing humidity. According to the characteristic experiments performed at the temperature of 80° C. under the conditions of the same impressed power supply, there are hardly any influences due to differences in temperature. As a result, in the temperature-humidity detecting element, the variations in the electric impedance depends upon the humidity only under the conditions where the low frequency power supply has been impressed.

Figure 11:
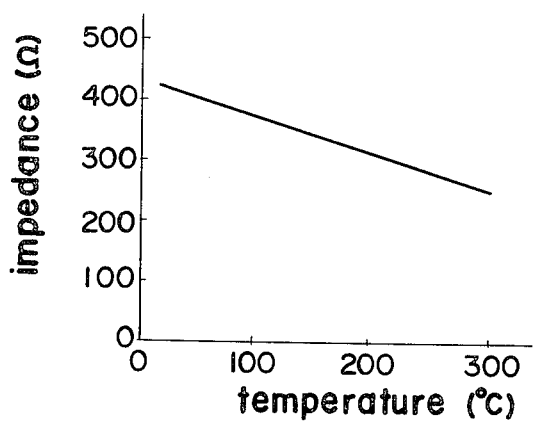
FIG. 11 shows a temperature detection characteristic graph upon the variations of electric impedance applied to the temperature-humidity detecting element in the above-noted further embodiment.
Figure 12:
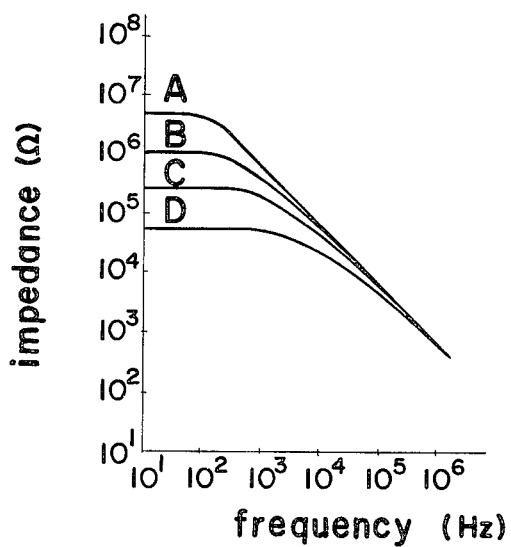
FIG. 12 shows a frequency characteristic graph upon the variations of the electric impedance applied to the temperature-humidity detecting element in the further embodiment.

The graph of FIG. 11 shows the variations in the electric impedance of the temperature-humidity detecting element accompanied by the variations in the temperature when the high frequency power supply of 1,000 KHz-1V has been applied between the both electrodes 3 and 3 in the humidity 50% RH at the temperature of 1° to 95° C. with a result such that the electric impedance varies in accordance with the variations in the temperature. Also, there are hardly any variations to the characteristics due to humidity changes even when the relative humidity has been made 10% (0° to 80° C.) and 90% (0° to 80° C) under the condition of the same applied power supply. The graph of FIG. 12 shows the frequency-electric impedance characteristics at the temperature of 20° C. when the humidity has been used as a parameter in such a manner that reference character A shows the characteristics with 20% RH in humidity, B with 40% RH in humidity, C with 60% RH in humidity, and D with 80% RH in humidity. No influences are shown due to the variations in the humidity in the high frequency zone.

From the above experimental results, it is to be noted that, in the temperature-humidity detecting element, the variation in the electric impedance depends upon the humidity under the low frequency power supply application conditions and the variations in the electric impedance depend upon the temperature under the high frequency power supply application conditions.

Since the composition of the temperature-humidity detecting element is not restricted to the component of the $PbTiO_3$, one type or plural types selected from among $BaTiO_3$, $SrTiO_3$, $CaTiO_3$, $PbZrO_3$, $KNbO_3$, $NaNbO_3$, $LiNbO_3$, $LiTaO_3$ and $Pb(Mg_{1/3}Nb_{2/3})O_3$ and other perobskite type, tungsten bronze type, pyroclower type, spinel type and metallic oxides can be added to $PbXO_3$ to provide an element, which is quicker in response, has a much less characteristic deterioration, has a higher sensitivity, and is superior in the temperature and humidity separation during the detection of the temperature and the humidity. Other additives can be added to control the characteristics so that the higher sensitivity may be provided within a limited humidity or temperature detecting range to the element. Also, the element of the present invention is superior in thermal resistance, and if and when the element is contaminated with suspended particles in the air, heating and cleaning operations can be performed to remove the contamination.

It is found out by the experiments that the same results can be obtained with a temperature-humidity detecting element with composition selected from among $KTaO_3$, $PbHfO_3$, $LiTaO_3$, $LiNbO_3$, $CaTiO_3$, $PbZrO_3$, $NaNbO_3$, and $KNbO_3$ to be employed in place of $PbTiO_3$ as a major component. The experimental results of the temperature and humidity characteristics of each of the temperature-humidity detecting elements will be shown hereinafter in the Table 2.

TABLE 2

| | | Humidity characteristics | 50% RH (1-95° C.) | Temperature characteristics | at 20° C. |
|---|---|---|---|---|---|
| Major Component | | ($\Omega$) 20° C. | 1MHz 150° C. | ($\Omega$) 20% RH | 10 Hz 80% RH |
| 22 | $PbTiO_3$ | 420 | 340 | $7.4 \times 10^6$ | $7.6 \times 10^4$ |
| 23 | $KTaO_3$ | 1050 | *1750 | $1.1 \times 10^7$ | $7.5 \times 10^4$ |
| 24 | $PbHfO_3$ | 2750 | 1000 | $6.3 \times 10^6$ | $8.1 \times 10^4$ |
| 25 | $LiTaO_3$ | 2800 | 2200 | $7.8 \times 10^6$ | $6.2 \times 10^4$ |
| 26 | $LiNbO_3$ | 2800 | 2100 | $7.0 \times 10^6$ | $2.4 \times 10^4$ |
| 27 | $CaTiO_3$ | 1100 | 1750 | $9.0 \times 10^6$ | $7 \times 10^4$ |
| 28 | $PbZrO_3$ | 2900 | 1500 | $1 \times 10^7$ | $9 \times 10^4$ |
| 29 | $NaNbO_3$ | 450 | 320 | $7.2 \times 10^6$ | $3 \times 10^4$ |
| 30 | $KNbO_3$ | 320 | 700 | $9.9 \times 10^6$ | $8.1 \times 10^4$ | remark:
*at 100° C. in place of 150° C.

Also, the same effects can be obtained if Ag, Ni, Zn, Cr, Pd, Au, Pt, Sn, Cu, Al, In, except for $RuO_2$ series, are applied through an electrode paste baking method, solution jetting method, evaporating method or the like as the electrode material of all the temperature-humidity detecting elements. In such method as described hereinabove, the electrode can be formed of metallic oxide, semiconductor, etc. each having nickel oxide, zinc oxide and indium oxide as a major component.

The element is not restricted, in size, hape and construction, to the above-noted embodiment and various other sizes and shapes can be utilized.

Hereinbelow is described one embodiment of the temperature-humidity detecting apparatus comprising: an element in which at least a pair of electrodes having terminals are provided on a portion composed of a dielectric, said dielectric varying in impedance in accordance with variations in the temperature and humidity in the atmosphere owing to the large temperature dependency of the dielectric constant and the large variation in resistance value upon the vapor absorption; a load impedance source whose impedance selectively varies in accordance with variations in frequency; and an oscillating circuit power source, said load impedance source and said oscillating circuit power source being connected in series with said electrode terminals, the temperature and humidity being detected by selecting respective oscillating frequencies of said oscillating circuit power source.

Figure 13:
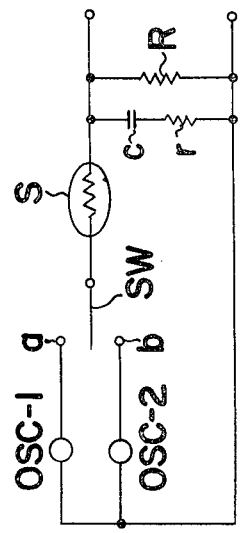
FIG. 13 is an electric circuit diagram of a temperature-humidity detecting apparatus in one embodiment of the present invention.

In FIG. 13, the above-described element 1 of $Ba_{0.5}Sr_{0.5}TiO_3$ series was used as the temperature-humidity detecting element S and an oscillator OSC-1 for 10 Hz-1V and an oscillator OSC-2 for 1 MHz-1V connected in parallel to each other are provided to connect to the element S by a change-over switch SW in series. A load impedance which can select a frequency is provided by a resistor (100K$\Omega$)R, a capacitor (1000pF)C and a resistor (1K$\Omega$)r, wherein the capacitor connected with the resistor r in series is connected in parallel with a resistor (100K$\Omega$)R and the combination connected in series with the element S and the power supply: the change-over switch SW is adapted to alternatively connect the oscillators OSC-1 and OSC-2 to the element S.

When the change-over switch SW is thrown to the "a" side, the oscillator OSC-1 is connected and an output signal is generated in accordance with humidity variations across the load impedance composed of resistors (R,r) and a capacitor (C). The load impedance when the oscillator OSC-1 side has been connected becomes predominantly R. When the changeover switch SW is thrown to the "b" side, the oscillator OSC-2 is connected and an output signal is generated in accordance with temperature variations across the load impedance composed of resistors (R,r) and a capacitor (C). The load impedance when the oscillator OSC-2 has been connected becomes predominantly r. The load impedance which selectively varies in accordance with variations in frequency therefore varies in value in dependence upon whether the temperature or humidity is to be detected. The circuit construction of the embodiment allows the detection to be made within the range of 0° to 200° C. in temperature and 10 to 99% RH in humidity. As described hereinabove, the temperature-humidity detecting apparatus allows one circuit construction to detect both the temperature and humidity.

Figure 14:
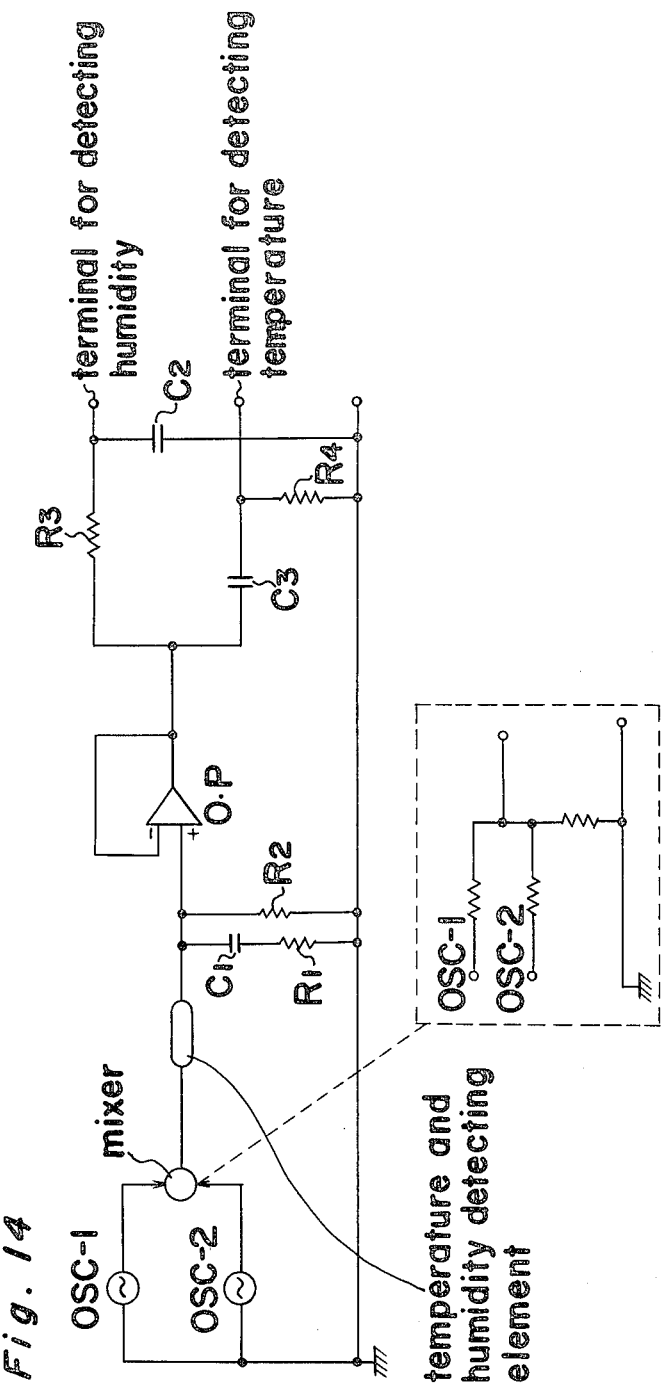
FIG. 14 is a similar view to FIG. 13 showing another embodiment of the temperature-humidity detecting apparatus.

FIG. 14 shows another embodiment of the temperature-humidity detecting apparatus according to the present invention. In FIG. 14, the pair of oscillators OSC-1 and OSC-2 are mixed by a mixer in place of the change-over switch SW of FIG. 13, and the load impedance which selectively varies in accordance with variations in frequency is composed of resistors (R1, R2) and a capacitor (C1). can be set to a value the load impedance desires.

To separate the detected frequency, a filter which is composed of, for example, resistors (R3, R4) and capacitors (C2, C3) is provided between a pair of detecting terminals and an operational amplifier connected to the load impedance. Such a circuit construction as described hereinabove can individually detect the temperature and humidity simultaneously at each of the terminals. In other words, the detected value of the temperature and humidity is outputted as variations in voltage at their respective output terminals. The temperature-humidity detecting apparatus of the embodiment allows the detection to be performed within the range of 0° to 200° C. in temperature and 10 to 99% RH in humidity as in the apparatus shown in FIG. 13.

As described hereinabove, the temperature-humidity detecting apparatus allows one circuit structure to detect the temperature and humidity at the same time. The apparatus for controlling the temperature and humidity of the present invention can be simplified in construction in the fields of air conditioning, weather, food industry, medical chemistry, etc., thus resulting in lower apparatus cost.

Also, it is found out by the experiments that the above-described temperature-humidity detecting apparatus of the present invention can detect the temperature and humidity with any of the above-described various temperature-humidity detecting elements.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A temperature-humidity detecting apparatus comprising:
    an element in which a pair of electrodes having terminals are provided on a dielectric portion, said dielectric varying in impedance in accordance with variations in the ambient temperature and humidity due to the large temperature dependency of the dielectric constant thereof and the large variation in resistance value due to the vapor absorption thereof;
    a load impedance whose impedance selectively varies in accordance with variations in frequency; and
    an oscillating circuit power source, said load impedance and said oscillating circuit power source being connected in series with said electrode terminals of said element, the temperature and humidity being detected by selecting respective oscillating frequencies of said oscillating circuit power source.

2. A temperature-humidity detecting apparatus as defined in claim 1, wherein said dielectric is an oxide having, as a major component thereof, a composition composed of a $Ba_{1-x}Sr_xTiO_3$ component with the composition range of $x=0$ to $1$.

3. A temperature-humidity detecting apparatus as defined in claim 1, wherein said dielectric is an oxide having, as a major component thereof, a component shown in $PbXO_3$, the X being a component containing at least one compound selected from among $(Mg_{1/2}W_{1/2})$, $(Cd_{1/2}W_{1/2})$, $(Co_{1/2}W_{1/2})$, $(Sc_{1/2}Nb_{1/2})$, $(Fe_{1/2}Nb_{1/2})$, $(In_{1/2}Nb_{1/2})$, $(Yb_{1/2}Nb_{1/2})$, $(Ho_{1/2}Nb_{1/2})$, $(Fe_{1/2}Ta_{1/2})$, $(Sc_{1/2}Ta_{1/2})$, $(Lu_{1/2}Nb_{1/2})$, $(Lu_{1/2}Ta_{1/2})$, $(Mg_{1/3}Nb_{2/3})$, $(Zn_{1/3}Nb_{2/3})$, $(Co_{1/3}Nb_{2/3})$, $(Ni_{1/3}Nb_{2/3})$, $(Mg_{1/3}Ta_{2/3})$, $(Co_{1/3}Ta_{2/3})$, $(Ni_{1/3}Ta_{2/3})$, $(Fe_{2/3}W_{1/3})$, $(Mn_{2/3}W_{1/3})$.

4. A temperature-humidity detecting apparatus as defined in claim 1, wherein said dielectric is an oxide having, as a major component thereof, a component shown in $ABO_3$, the AB being a component containing at least one compound selected from among KTa, PbHf, LiTa, LiNb, CaTi, PbZr, NaNb, KNb, PbTi.

* * * * *